United States Patent
Edic et al.

(10) Patent No.: US 7,366,279 B2
(45) Date of Patent: Apr. 29, 2008

(54) SCATTER CONTROL SYSTEM AND METHOD FOR COMPUTED TOMOGRAPHY

(75) Inventors: Peter Michael Edic, Albany, NY (US); Bruno Kristiaan Bernard De Man, Clifton Park, NY (US); Mark Ernest Vermilyea, Niskayuna, NY (US); Christopher David Unger, Brookfield, WI (US); John Eric Tkaczyk, Delanson, NY (US); James Walter LeBlanc, Niskayuna, NY (US); Samit Kumar Basu, Niskayuna, NY (US); William Robert Ross, Scotia, NY (US); Jonathan David Short, Clifton Park, NY (US); Scott Stephen Zelakiewicz, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 275 days.

(21) Appl. No.: 10/903,298

(22) Filed: Jul. 29, 2004

(65) Prior Publication Data

US 2006/0023832 A1 Feb. 2, 2006

(51) Int. Cl.
*A61B 6/03* (2006.01)

(52) U.S. Cl. ........................ 378/7; 378/150; 378/151; 378/154

(58) Field of Classification Search ............ 378/7–10, 378/92, 145–155, 160–161, 204, 210, 910, 378/901
See application file for complete search history.

(56) References Cited

U.S. PATENT DOCUMENTS

| | | | | |
|---|---|---|---|---|
| 4,126,786 A | * | 11/1978 | LeMay et al. | 378/7 |
| 4,203,036 A | * | 5/1980 | Tschunt | 378/9 |
| 4,315,157 A | * | 2/1982 | Barnes | 378/10 |
| 5,165,100 A | * | 11/1992 | Hsieh et al. | 382/131 |
| 5,394,452 A | * | 2/1995 | Swerdloff et al. | 378/65 |
| 5,485,493 A | * | 1/1996 | Heuscher et al. | 378/15 |
| 6,396,898 B1 | * | 5/2002 | Saito et al. | 378/19 |

OTHER PUBLICATIONS

US Patent Application 127068-2, U.S. Appl. No. 10/816,064, filed Apr. 1, 2004.
US Patent Application 134435, U.S. Appl. No. 10/704,179, filed Nov. 7, 2003.

* cited by examiner

*Primary Examiner*—Edward J. Glick
*Assistant Examiner*—John M Corbett
(74) *Attorney, Agent, or Firm*—Jason K. Klindtworth; Curtis B. Brueske

(57) ABSTRACT

Various configurations for scatter reduction and control are provided for CT imaging. These configurations include an imaging system having a stationary detector extending generally around a portion of an imaging volume and a distributed X-ray source placed proximal to the stationary detector for radiating an X-ray beam toward the stationary detector. A scatter control system is further provided that is configured to adaptively operate in cooperation with the stationary detector and the distributed X-ray source to focally align collimator septa contained therein to the X-ray beam at a given focal point and to provide X-ray beam scatter control.

20 Claims, 12 Drawing Sheets

SCATTER CONTROL SYSTEM AND METHOD FOR COMPUTED TOMOGRAPHY

BACKGROUND OF THE INVENTION

The present invention relates generally to the field of computed tomography imaging systems. In particular, the invention relates to methods and systems for scatter control and reduction in a stationary computed tomography (SCT) system.

Computed tomography (CT) imaging systems have been developed over the past decades and now are prolific in medical diagnostics and other contexts. In general, such systems typically include an X-ray source, such as a conventional X-ray tube, positioned diametrically opposed to an X-ray detector. In a so-called third generation CT system design, the source and detector rotate on a gantry, and the source is triggered repeatedly or is on continuously during rotation to produce beams of X-ray radiation that are directed through a subject of interest and fall onto the detector on the opposite side of a gantry. Features and structures of the subject attenuate the emitted radiation, and the detector measures the transmitted radiation. The measurements are usually converted to attenuation measurements and the resulting measurement or projection data are then processed for reconstruction of useful images, typically presented as slices or images through the subject. Many such images may be produced in a single imaging sequence.

Next generation CT architectures, which include stationary computed tomography (SCT) concepts, offer high effective scan speeds by using distributed, stationary, addressable electron emitters to rapidly trigger electron beams onto a stationary, distributed X-ray target, thereby producing X-rays. The X-rays after traversing a subject of interest are collected by a stationary, distributed X-ray detector. SCT systems offer various advantages over the conventional CT systems.

Detectors for conventional CT systems using rotating gantries are becoming increasingly larger with small detector cells for improved imaging resolution, utilizing multiple rows to obtain significant axial coverage on the object of interest during an exam or scan. Circuitry associated with the detectors must also be rotated to perform the data acquisition and initial processing. Thus having a stationary detector and/or a stationary source in a SCT design lightens rotational loads, or even eliminates the need for rotation of system components all together. These systems are useful for generating high-quality images while reducing the mechanical, electrical, and thermal challenges associated with rotation of a source and a detector in a conventional CT system.

Though current CT imaging systems and SCT designs are very useful in identifying features of interest within a subject, they pose certain limitations. When a CT or SCT imaging system is operated, the passage of X-rays through an object results in a combination of photoelectric absorption, coherent scattering, and Compton scattering. In the CT and SCT imaging systems, it is the pattern of transmitted X-rays through the object that is useful for reconstructing an image of the object's interior structure. The scatter component degrades image quality in resulting reconstructions. Scatter in the measured data results in image artifacts and increases noise in the measurements, even if the scatter is accurately estimated and eliminated through special correction algorithms. Scatter artifacts can be mitigated by subtracting an estimate of the scatter, but the signal to noise ratio (SNR) cannot be recovered by scatter correction.

The X-ray beam used with most CT imaging systems for large volume coverage has a large cone angle; therefore, the amount of scattered radiation in the measurements increases. In conventional CT systems utilizing rotating gantries, an anti-scatter grid, sometimes referred to as a collimator, is placed in front of the detector, which selectively attenuates scattered X-rays but allows primary X-rays to reach the detector. Although the collimator plates are designed to have little effect on the transmission of the primary X-ray beam, they do attenuate it to some extent due to their finite cross-section. As individual CT detectors sizes get smaller, a larger fraction of the area of each pixel is shadowed by the collimator blade, leading to poor dose utilization—a smaller amount of dose applied to the patient is detected and used for diagnostic imaging purposes. The drawback of reducing the active area of the X-ray detector as sizes get smaller (since the collimator blades cover a larger portion of the active area) has been addressed primarily by making thinner collimator plates, which poses significant manufacturing and reliability challenges. There is a physical limit to how thin the collimator blades can be manufactured while still maintaining their utility.

So-called fourth generation CT scanners use a fixed array of detectors and a rotating X-ray source. SCT imaging systems use a fixed array of detectors and one or more addressable, distributed X-ray sources positioned around the patient. The distributed X-ray sources are activated at varying times and in various sequences. Because a given individual, stationary detector measures X-rays from a large number of source directions, it is difficult to use a collimator to reject scattered radiation, which leads to reduced image quality. As mentioned above with conventional CT systems, an anti-scatter grid, which allows primary photons to be detected, may accompany the detector to reduce measurement of scattered photons. In SCT designs, a scatter grid fixed to the detector is no longer possible, because every detector cell needs to have a wide acceptance angle to appropriately measure the transmitted primary radiation from a number of distributed X-ray source positions.

There is a continuing need, therefore, for improvements in CT imaging systems that can effectively reduce scatter and optimize patient dose efficiency. There is, at present, a particular need for improved system designs for SCT applications that permit measurement of data with higher fidelity.

SUMMARY OF THE INVENTION

The present invention provides novel techniques, which reduce scatter in X-ray measurements, provide better dose utilization, and provide projection data with improved fidelity. While presently contemplated applications for these systems include diagnostic medical imaging applications, the new techniques may find varied applications outside the medical diagnostics context, including part inspection, parcel and package handling and screening, baggage scanning, and so forth. In general, the techniques of the present invention reduce scatter, improve the dose efficiency, and/or improve the quality of the measurement data.

According to one aspect of the present technique, an imaging system is provided that includes a stationary detector extending generally around a portion of an imaging volume, and, a distributed X-ray source placed proximal to the stationary detector for radiating an X-ray beam toward the stationary detector. The imaging system also includes a scatter control system configured to adaptively operate in cooperation with the stationary detector and the distributed X-ray source to provide X-ray beam scatter control.

According to another aspect of the present technique, a method of imaging is provided that includes the sequential firing of a distributed X-ray source for directing an X-ray beam toward a stationary detector; and using a scatter control system in cooperation with the stationary detector and the distributed X-ray source.

DETAILED DESCRIPTION OF SPECIFIC EMBODIMENTS

Figure 1:
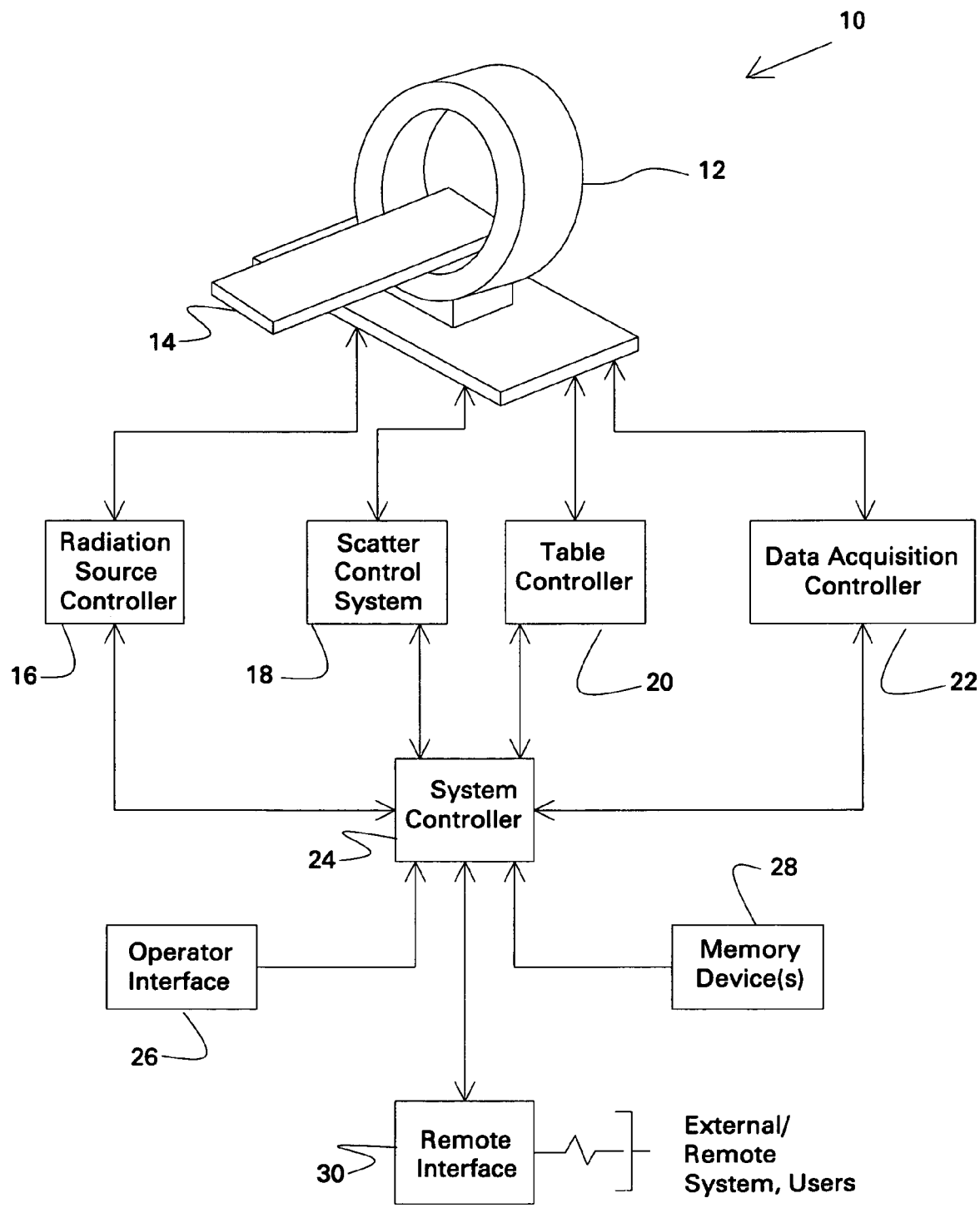
FIG. 1 is a diagrammatical representation of an exemplary CT system in accordance with aspects of the present technique.

Turning now to the drawings, referring first to FIG. 1, a computed tomography (CT) system is illustrated and designated generally by reference numeral 10. The CT system 10 comprises a gantry 12 formed of a support structure and internally containing one or more stationary or rotational, distributed sources of an X-ray radiation (not shown in FIG. 1) and one or more stationary or rotational X-ray detectors (not shown in FIG. 1), as described in greater detail below. The gantry 12 is configured to receive a table 14 or other support for a patient (not shown), or, more generally, a subject to be scanned. The table can be moved through an aperture in the scanner to appropriately position the subject in an imaging volume or scanning plane during imaging sequences.

The system further includes a radiation source controller 16, a scatter control system 18, a table controller 20 and a data acquisition controller 22, which may all function under the direction of a system controller 24. The radiation source controller 16 regulates the addressing, timing, duration, and generation of X-ray radiation (not shown) which is directed from points around the gantry 12 toward a detector segment (not shown) on an opposite side thereof, as discussed below. In the present stationary CT arrangements, the radiation source controller 16 may trigger one or more electron emitters in a distributed X-ray source at each instant in time for creating multiple measurements of projection data. In certain arrangements, for example, the X-ray radiation source controller 16 may trigger emission of radiation in sequences so as to collect spatially adjacent or non-adjacent projection data around the gantry. Many such projection data may be collected in an examination sequence, and the data acquisition controller 22, coupled to detector elements as described below, receives signals from the detector elements and processes the signals for storage and later image reconstruction. In configurations described below in which one or more distributed X-ray sources may be stationary or rotational, source controller 16 may also direct rotation of a gantry on which the distributed source or sources are mounted.

The scatter control system 18, in an exemplary embodiment, is configured to adaptively operate in cooperation with the distributed X-ray source and the stationary detector. The scatter control system 18 focally aligns the scatter rejection hardware with X-ray radiation emitted by the source and appropriately collimates each detector element. According to different aspects of the present technique described in more detail below, the scatter control system operates such that the scattered radiation is effectively reduced. As used herein, scatter control and reduction are used interchangeably and include reduction, rejection or limitation of scatter. Table controller 20 serves to appropriately position the table and subject thereupon in a plane in which the X-ray radiation is emitted, or, in the present context, generally within a volume to be imaged. The table may be displaced between imaging sequences or during certain imaging sequences, depending upon the imaging protocol employed.

System controller 24 generally regulates the operation of the radiation source controller 16, the scatter control system 18, the table controller 20 and the data acquisition controller 22. The system controller 24 may thus cause radiation source controller 16 to trigger emission of X-ray radiation, as well as to coordinate such emissions during imaging sequences defined by the system controller. The system controller may also regulate movement of the table in coordination with such emission so as to collect measurement data corresponding to particular volumes of interest, or in various modes of imaging, such as helical or axial imaging modes. Moreover, system controller 24 coordinates rotation of a gantry 12 on which the source(s) and embodiments of the scatter control system may be mounted, if needed. The system controller 24 also receives data acquired by data acquisition controller 22 and coordinates storage and processing of the data.

It should be borne in mind that the controllers, and indeed various circuitry described herein, may be defined by hardware circuitry, firmware or software. The particular protocols for imaging sequences, for example, will generally be defined by code executed by the system controller. Moreover, initial processing, conditioning, filtering, and other operations required on the measurement data acquired by the CT system may be performed in one or more of the components depicted in FIG. 1. For example, as described below, detector elements in a diode arrangement will produce analog signals representative of charge generated in the photodiodes positioned at locations corresponding to pixels of the data acquisition detector. Such analog signals are converted to digital signals by electronics within the scanner, and are transmitted to data acquisition controller 22. Partial processing may occur at this point, and the signals ultimately transmitted to the system controller for further filtering and processing. Other such detector technology is equally suitable for embodiment of the detector, such as direct conversion devices, photon counting devices, or energy discriminating photon counting systems.

System controller 24 is also coupled to an operator interface 26 and to one or more memory devices 28. The operator interface may be integral with the system controller, and will generally include an operator workstation for initiating imaging sequences, controlling such sequences, and manipulating measurement data acquired during imaging sequences. The memory devices 28 may be local to the imaging system, or may be partially or completely remote from the system. Thus, memory devices 28 may include local, magnetic or optical memory, or local or remote repositories for measured data for reconstruction. Moreover, the memory devices may be configured to receive raw, partially processed or fully processed projection data for reconstruction.

System controller 24 or operator interface 26, or any remote systems and workstations, may include software for image processing and reconstruction. As will be appreciated by those skilled in the art, such processing of CT measurement data may be performed by a number of mathematical algorithms and techniques. For example, conventional filtered back-projection techniques may be used to process and reconstruct the data acquired by the imaging system. Other techniques used in conjunction with filtered back-projection may also be employed. A remote interface 30 may be included in the system for transmitting data from the imaging system to such remote processing stations or memory devices.

Figure 2:
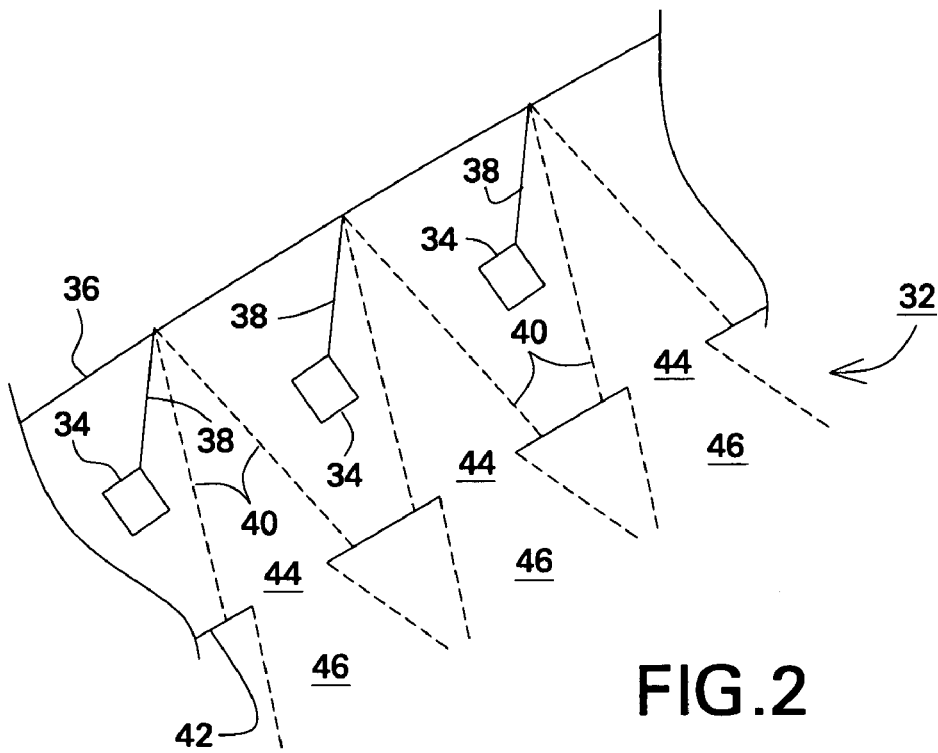
FIG. 2 is a diagrammatical representation of an exemplary distributed source for use with a system of the type illustrated in FIG. 1.

The gantry 12 of CT system 10 preferably includes one or more rotating or stationary distributed X-ray sources as well as one or more stationary detectors for receiving transmitted X-ray radiation and processing corresponding signals to produce measurement data. FIG. 2 illustrates a portion of an exemplary distributed X-ray source of the type that may be employed in the CT system 10. As shown in FIG. 2, in an exemplary implementation, the source 32' may include a series of electron beam emitters 34 that are coupled to radiation source controller 16 shown in FIG. 1, and are triggered by the source controller during operation of the scanner. The electron beam emitters 34 are positioned adjacent to a distributed target 36. Upon triggering by the source controller, the electron beam emitters 34 may emit electron beams 38 toward target 36. The target 36, which may, for example, be a tungsten rail or element, emits X-ray radiation, as indicated at reference numeral 40, upon impact of the electron beams. In reflection mode, X-rays are produced primarily on the same side of the target as where the electrons impact. In transmission mode, X-rays are produced at the opposite side of the impact location of the electron beam on the target. The X-ray beams 40 are directed, then, toward collimator septa 42, which are generally opaque to the X-ray radiation, but which include openings or apertures 44. The apertures 44 may be fixed in dimension, or may be adjustable. Although not shown, the collimator septa 42 may limit apertures 44 and thus define the in-plane fan angle or the longitudinal cone angle of the emitted X-ray beam. Apertures 44 permit a portion of the X-ray beams to penetrate through the collimator to form collimated beams 46 that will be directed to the imaging volume of the CT system, through the subject of interest, and that will impact detector elements on an opposite side of the scanner.

A number of alternative configurations for electron emitters or distributed sources may, of course, be envisaged. Moreover, the individual X-ray sources in the distributed source may emit various types and shapes of X-ray beams. These may include, for example, fan-shaped beams, cone-shaped beams, and beams of various cross-sectional geometries. Similarly, the various components comprising the distributed X-ray source may also vary. In one embodiment, for example, a cold cathode electron emitter is envisaged which will be housed in a vacuum housing. A stationary anode is then disposed in the housing and spaced apart from the emitter. This type of arrangement generally corresponds to the diagrammatical illustration of FIG. 2. Other materials, configurations, and principals of operations may, of course, be employed for the distributed source. The emission devices may be one of many available electron emission devices, for example, thermionic emitters, carbon-based emitters, photo emitters, ferroelectric emitters, laser diodes, monolithic semiconductors, etc.

The present CT techniques may use a plurality of distributed and addressable sources of X-ray radiation. Moreover, the distributed sources of radiation may be associated in single unitary enclosures or tubes, or in a plurality of tubes designed to operate in cooperation. The individual sources are addressable independently and separately so that radiation can be triggered from each of the sources at points in time during the imaging sequence as defined by the imaging protocol. Where desired, more than one such source may be triggered concurrently at any instant in time, or the sources may be triggered in specific sequences to mimic rotation of a gantry, or in any desired sequence around the imaging volume or plane. Also, it would be appreciated by those skilled in the art that sequentially firing or sequentially triggering the sources as described in the embodiments below could be done in random, in series, or in a particular configuration for example triggering the source locations that are 120 degrees apart.

Figure 3:
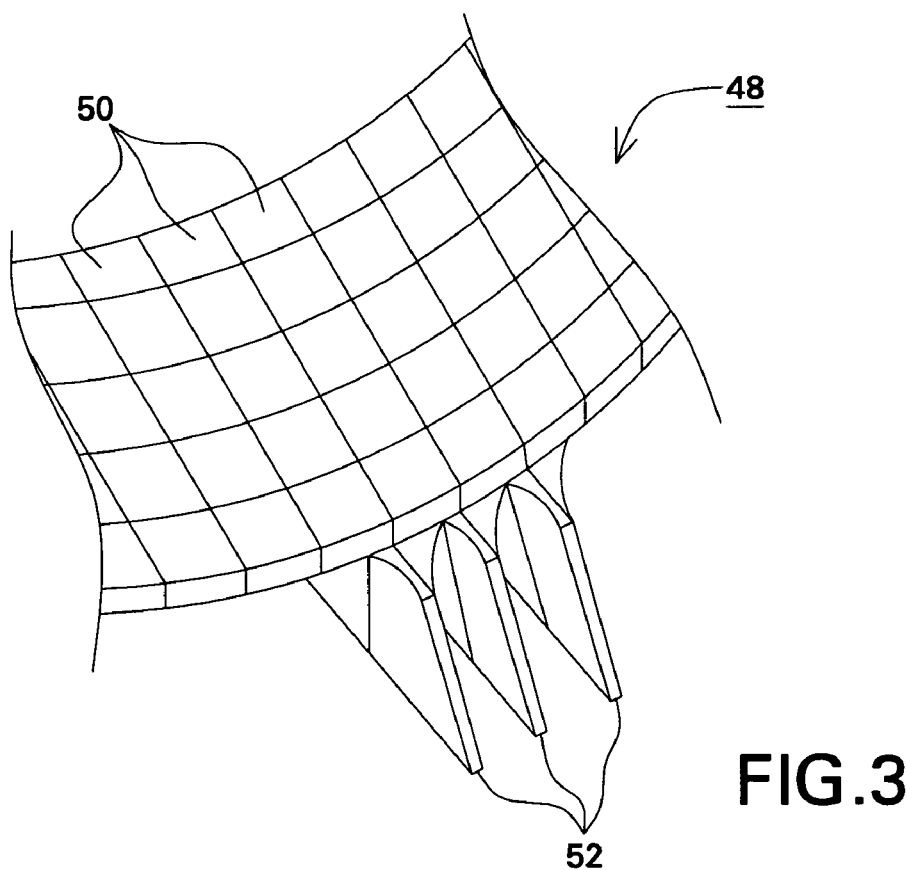
FIG. 3 is a diagrammatical representation of a portion of detector for use with the system illustrated in FIG. 1.

A plurality of detector elements forms one or more stationary detectors, which receive the radiation emitted by the distributed X-ray sources. FIG. 3 illustrates a portion of a stationary detector, which may be employed for the present purposes. The detector arrangement may be extended around a greater portion or the entire inner surface of the gantry 12 in FIG. 1 in certain embodiments. Each detector may be composed of detector elements with varying resolution to satisfy a particular imaging application. In general, however, the detector 48 includes a series of detector elements 50 and associated signal processing circuitry 52. These detector elements may be of one, two or more sizes, resulting in different spatial resolution characteristics in different portions of the measurement data. Each detector element may include an array of photodiodes. X-ray radiation impacting the detectors is converted to lower energy photons by a scintillator and these photons impact the photodiodes. By measuring the charge generated in the various photodiodes, each of which corresponds to a pixel in the collected data for each acquisition, data is collected that indirectly encodes radiation attenuation at each of the detector pixel locations. This data is processed by the signal processing circuitry 52, which will generally convert the analog depletion signals to digital values, may perform any necessary filtering, and will transmit the acquired data to processing components of the imaging system as described above.

A large number of detector elements 50 may be associated in the detector so as to define many rows and columns of pixels. The detector configurations of the present technique position detector elements across from independently addressable distributed X-ray sources so as to permit a large number of views to be collected for image reconstruction. Although the detector is described in terms of a scintillator-based energy-integrating device, direct conversion, photon counting, or energy discriminating detectors are equally suitable.

As will be appreciated by those skilled in the art, reconstruction techniques in CT systems vary in their use of acquired data, and in their techniques and assumptions for image reconstruction. It has been found, in the present technique, that a number of scatter control and reduction configurations are available which provide effective measurement of useful data for accurate image reconstruction while significantly reducing the mechanical complexity of the CT system, particularly on the gantry and support structures. FIGS. 4-13 illustrate exemplary geometries and configurations for distributed sources and for stationary detectors with effective scatter reduction and control techniques, which can be used with conventional or improved image processing and image reconstruction algorithms.

Figure 4:
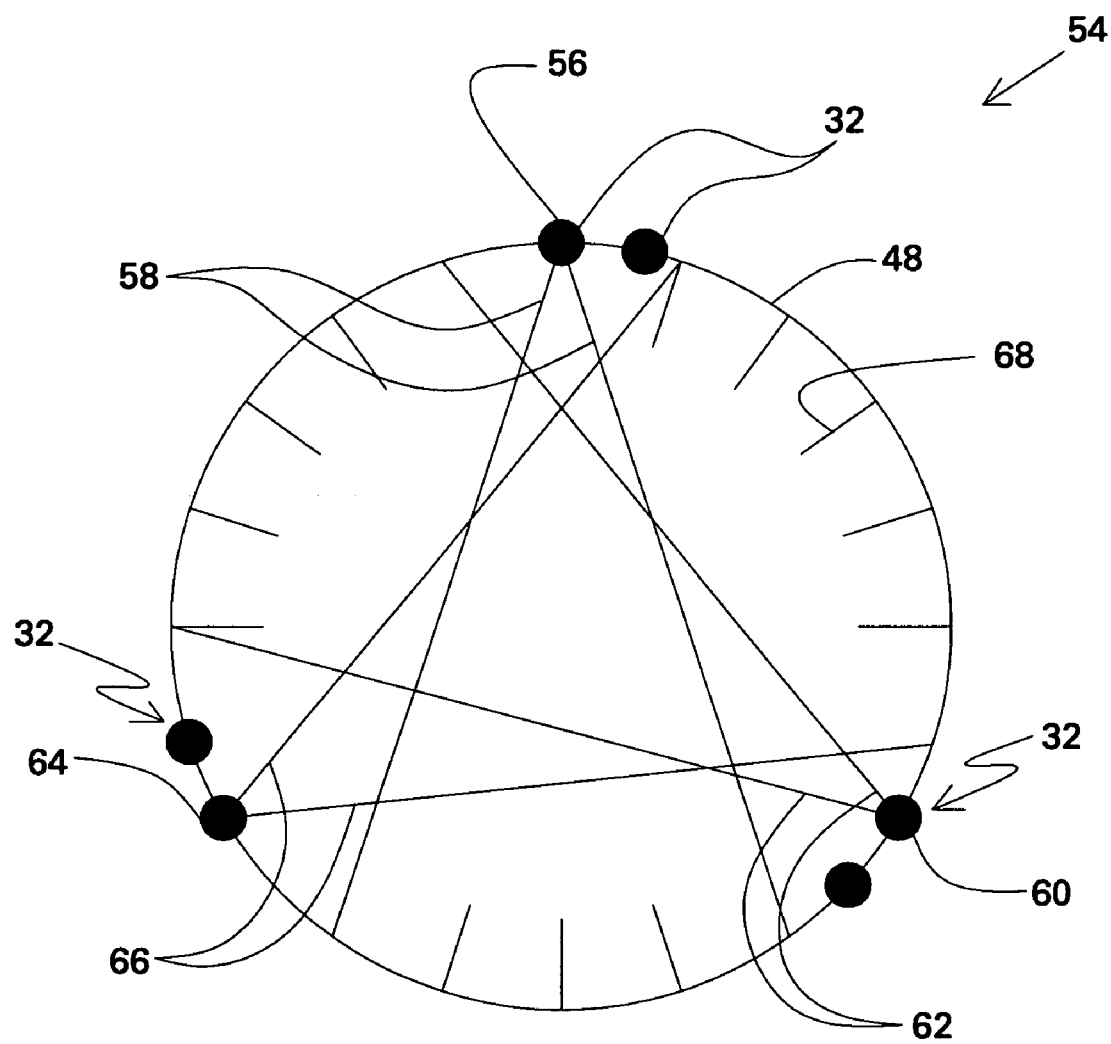
FIG. 4 is a diagrammatical representation of a first exemplary SCT system configuration, including an anti-scatter grid that is capable of being directed towards multiple focal points.

FIG. 4 is a diagrammatical representation of a first exemplary SCT system configuration, where the scatter control system 18 as described in FIG. 1 includes an anti-scatter grid 54 with multiple focal points, illustrated as 56, 60, and 64. The anti-scatter grid 54 may be disposed about the inner surface of the stationary detector 48 in FIG. 3 or may have a separate fixture altogether. Also the anti-scatter grid may be configured to be stationary or rotating with respect to the stationary detector, in accordance with different aspects of the present technique. The anti-scatter grid 54 including multiple collimator septa 68, as illustrated, is advantageously adapted to focally align septa 68 with the X-ray beams (58, 62, 66) from multiple source locations or focal spot locations (32), i.e. from multiple focal points 56, 60 and 64 as illustrated. The anti-scatter grid 54, in an exemplary embodiment is configured to rotate with respect to the stationary detector 48. The collimator septa as used herein, generally means a dividing or separating wall, a membrane, plate, or any other structure to separate bodily spaces or masses or volumes. Although collimation of three source positions are shown in FIG. 4, one or more source locations may be collimated in a similar fashion.

Figure 5:
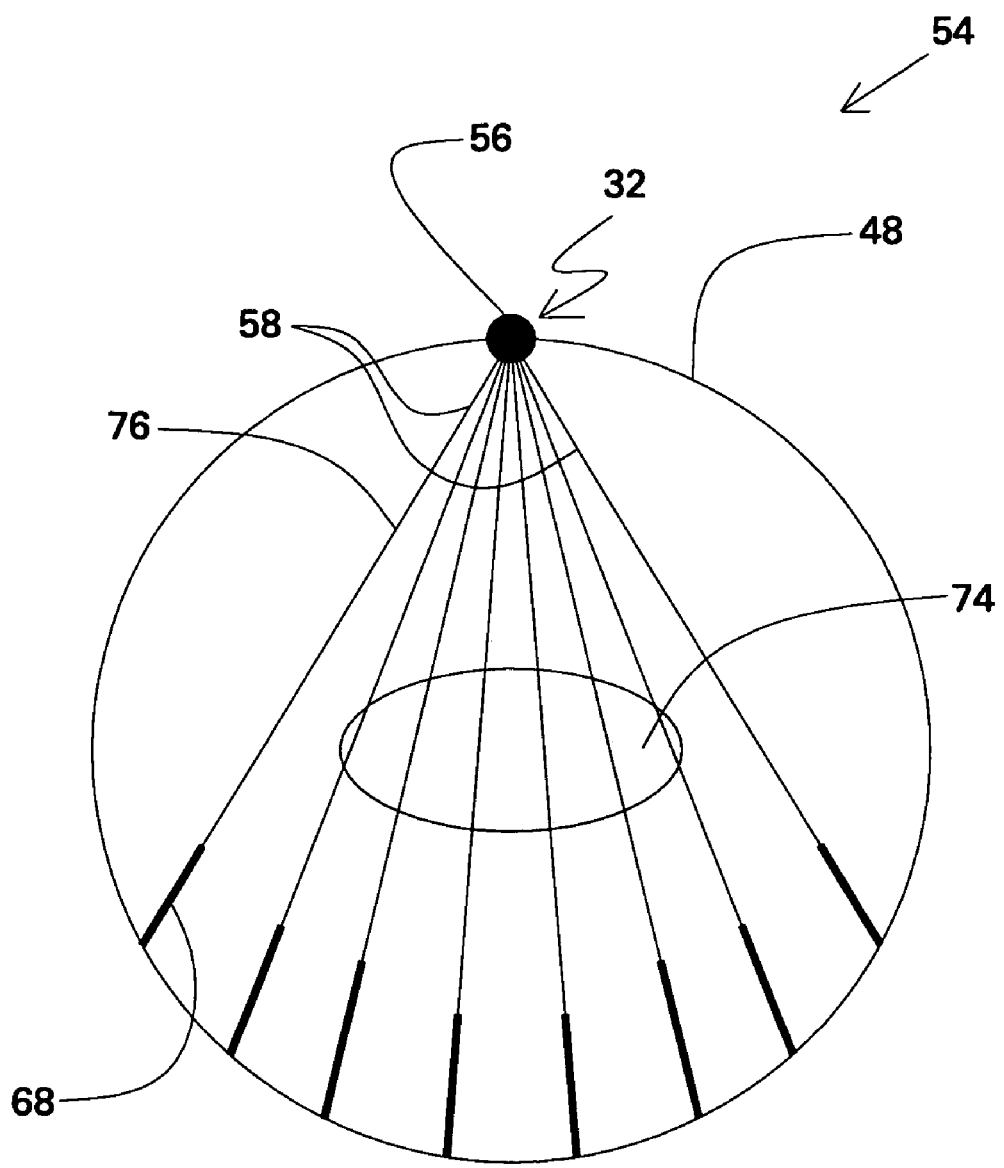
FIG. 5 is a diagrammatical representation of a further configuration, including an anti-scatter grid and an instantaneous addressable source point.

Under operation, as illustrated in FIG. 5, the distributed X-ray source comprising a focal spot location 32 located at a focal point position 56, for example, from amongst the multiple focal point positions is configured to be fired for an instantaneous field of view, which is defined by an area (or volume in three dimensions) swept by the X-ray beam 58. The detector 48 is stationary, but the anti-scatter grid 54 rotates, in one exemplary embodiment, so that its focal point 56 aligns with the focal spot location 32 that is fired at a given time instant. Thus, each of collimator septa 68 arranged around at least a portion of the detector 48 are aligned with each of the rays 76 of the primary X-ray beam 58. In one example, the anti-scatter grid 54 may be rotated at a constant speed, and for every measurement of projection data from the object 74 being imaged, the focal spot 32 that is at the focal point 56 of the anti-scatter grid 54 is fired. In another example, septa 68 may be positioned entirely around the gantry 12 in FIG. 1 and each third of the anti-scatter grid 54 may have a focal point 56 that aligns with a focal spot location 32 that will generate X-ray radiation. Using multiple focal points for different parts of the grid 54 makes it compatible with different imaging protocols, non-limiting examples include multi-spot mode (multiple spots are operated in an "on" mode simultaneously), and optimized time-sequential sampling (adjacent source points are not triggered sequentially, but operate in a sequence to optimize image quality for a certain application, for example cardiac imaging).

Figure 6:
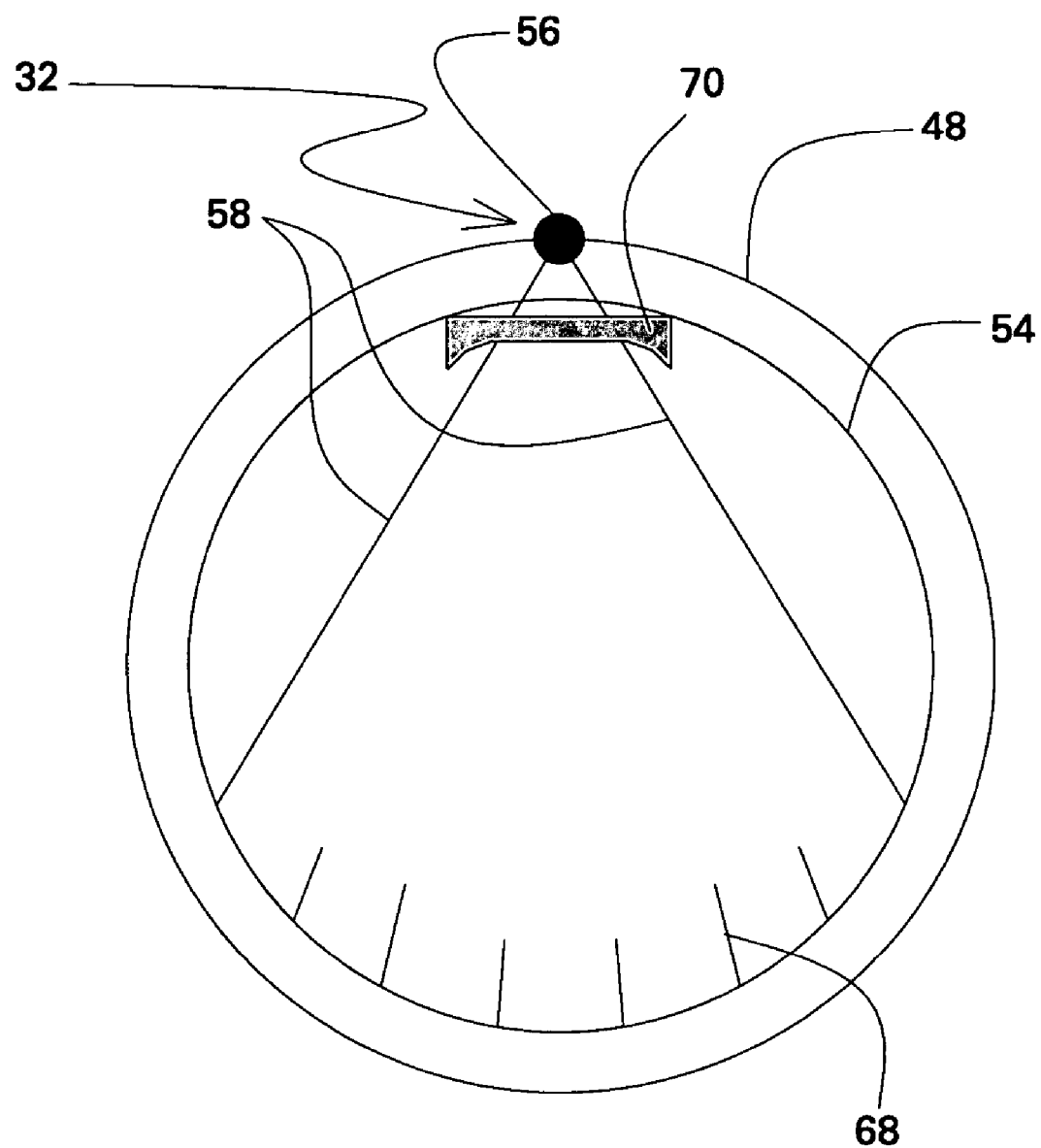
FIG. 6 is a diagrammatical representation of a further configuration, including a bowtie filter with the anti-scatter grid of FIG. 5.

FIG. 6 is a diagrammatical representation of a further embodiment, including a bowtie filter 70 arranged across from the collimator septa 68 of the anti-scatter grid 54. In one example, the bowtie filter 70 and the X-ray focal spot location 32 may be synchronized to shape the at least one X-ray beam 58 emitted from the X-ray focal spot location 32. In a specific example, there may be a rotating assembly attached with the bowtie filter 70 for achieving synchronization with the X-ray sources. A triggering mechanism may be used to ensure the bowtie filter 70, and X-ray focal spot location 32, are synchronized. It will be appreciated by those skilled in the art that the bowtie filter 70 may be used in conjunction with or separately from the collimator septa 68. When used in conjunction with the collimator septa 68, the bowtie filter 70 will shape the X-ray beam 58 that is generated by X-ray focal spot location 32. The X-ray beam 58 is also aligned with collimator septa 68 having a focal point 56 (coincident with focal spot location 32). In alternate configurations, at least one of the bowtie filter 70 and the collimator septa 68 rotate about the gantry 12 in FIG. 1. Furthermore, one or more bowtie filters 70 may be utilized to shape the X-ray beams from multiple focal spot locations 32 in either a stationary or rotating configuration.

Figure 7:
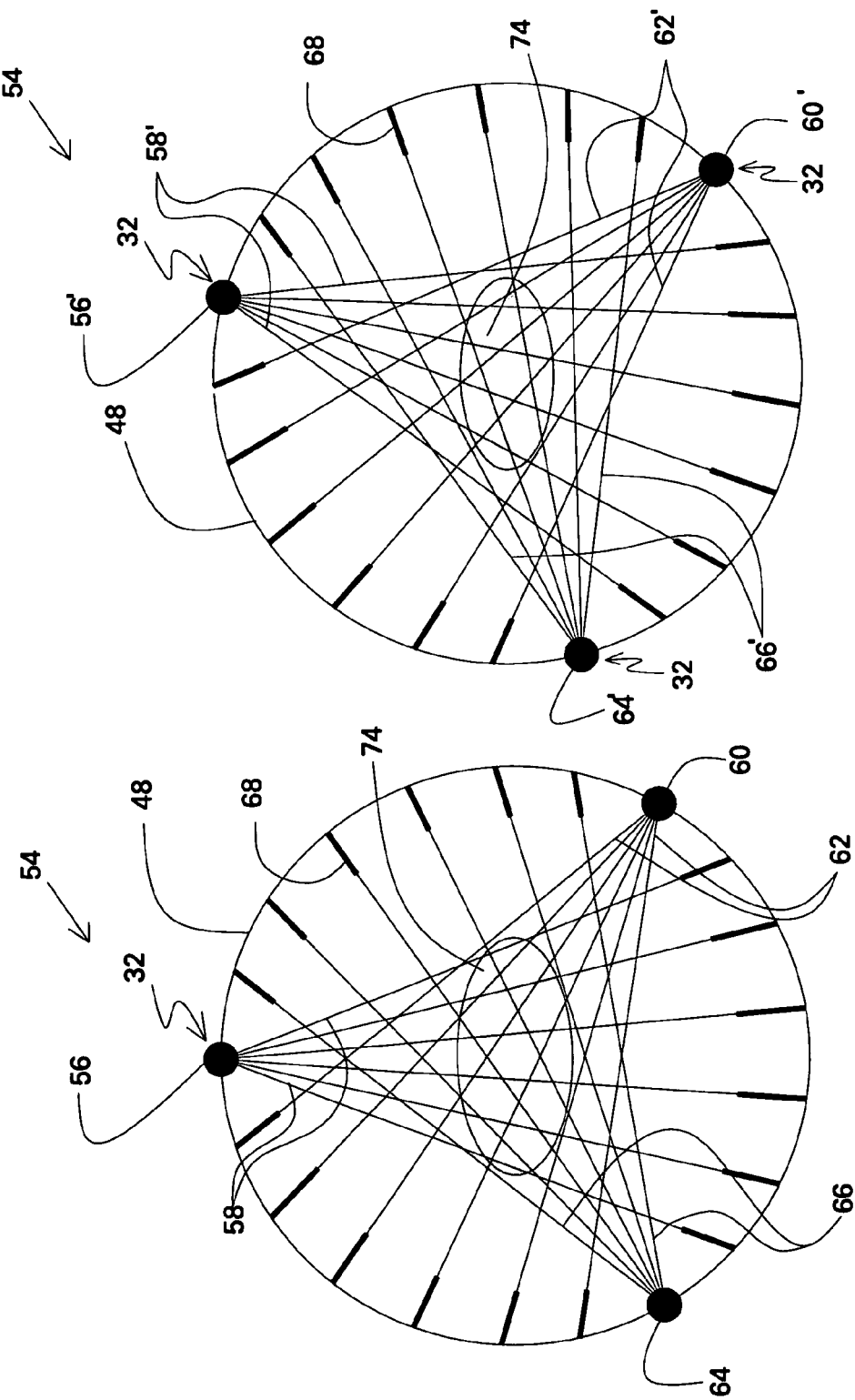
FIG. 7 is a diagrammatical representation of a further configuration with a plurality of collimator septa of varying angular positions in the anti-scatter grid of FIG. 4 and FIG. 5.

FIG. 7 is a diagrammatical representation of yet another embodiment in which the anti-scatter grid 54 is in a fixed or stationary position disposed about the inner surface of the stationary detector 48, and includes multiple collimator septa 68 located substantially around the detector 48. The multiple collimator septa 68, in an exemplary configuration, are angularly adjusted to ensure focal alignment, as the focal spot location 32 moves around an imaging volume 74, in the conventional CT systems, or alternatively as the sequential focal spot locations 32 are addressed in the stationary CT systems, as shown in FIG. 7. As sequential focal spot locations become active, the angular positions of collimator septa 68 adjust so that the collimator septa 68 are focally aligned with the respective focal spot location. Thus, in order to ensure focal alignment, the collimator septa 68 track the focal spot locations as illustrated by the left and right side illustrations in FIG. 7. As the X-ray focal spot location 32 moves (coincident with focal point 56 as shown on left, to coincidence with focal point 56' as shown on right), the collimator septa within the range of the beam 58 and 58' respectively, adjust angularly so that focal alignment is maintained. Similarly, as the focal spot locations 32 associated with focal points 56, 60, and 64 as shown on the left, move to focal points 56', 60', and 64' respectively on the right, the collimator septa within a respective range of beams 58, 62, and 66 and within a respective range of beams 58', 62' and 66', angularly adjust to maintain focal alignment. In one exemplary embodiment, one or more collimator septa that are not within an X-ray beam path may be configured to angularly adjust to prepare for full illumination of an instantaneous field of view for subsequent X-ray focal spot locations 32. Thus there may be a set of septa within the range of the instantaneous field of view that angularly adjust to maintain focal alignment with the focal spot location 32, and the remaining septa not within the instantaneous field of view that angularly adjust to a different angle, to prepare for full illumination of the instantaneous field of view for subsequent X-ray source locations. An analogy for this configuration may be kelp, as found on a sea or ocean floor in which the individual kelp branches change their orientation in concert with the tide. The multiple collimator septa as described hereinabove, in one example may be composed of high atomic number material and maybe of constant length. It will be well understood by those skilled in the art, that focal spot location 32 may exist either in a rotating source or a stationary source. As shown in FIG. 7, a collimation scheme may also be implemented to account for illuminating multiple X-ray source positions at one time, considerably reducing effective scan time and improving temporal resolution in CT imaging, especially for applications in cardiac imaging. In a more specific example, the radius of the X-ray source locations coincident with focal points 56, 60, 64, may match the radius of the detector ring 48, in which case the angular rotation of the collimator septa 68 from one X-ray focal spot location 32 to an angularly adjacent focal spot location 32 is constant (assuming equally spaced source points around the gantry). As a result, a mechanism that causes an increment in angular position for collimator septa within the X-ray beam enables implementation of this configuration. In one embodiment, a geared assembly (not shown) is attached to the collimator septa and increments the angular position of all collimator septa simultaneously—the position of each depending on the X-ray focal spot location. Although collimation of three X-ray focal spot locations are shown in FIG. 7, one or more X-ray focal spot locations 32 may be collimated to reduce scatter in measurements of the projection data from the instantaneous field of view.

Figure 8:
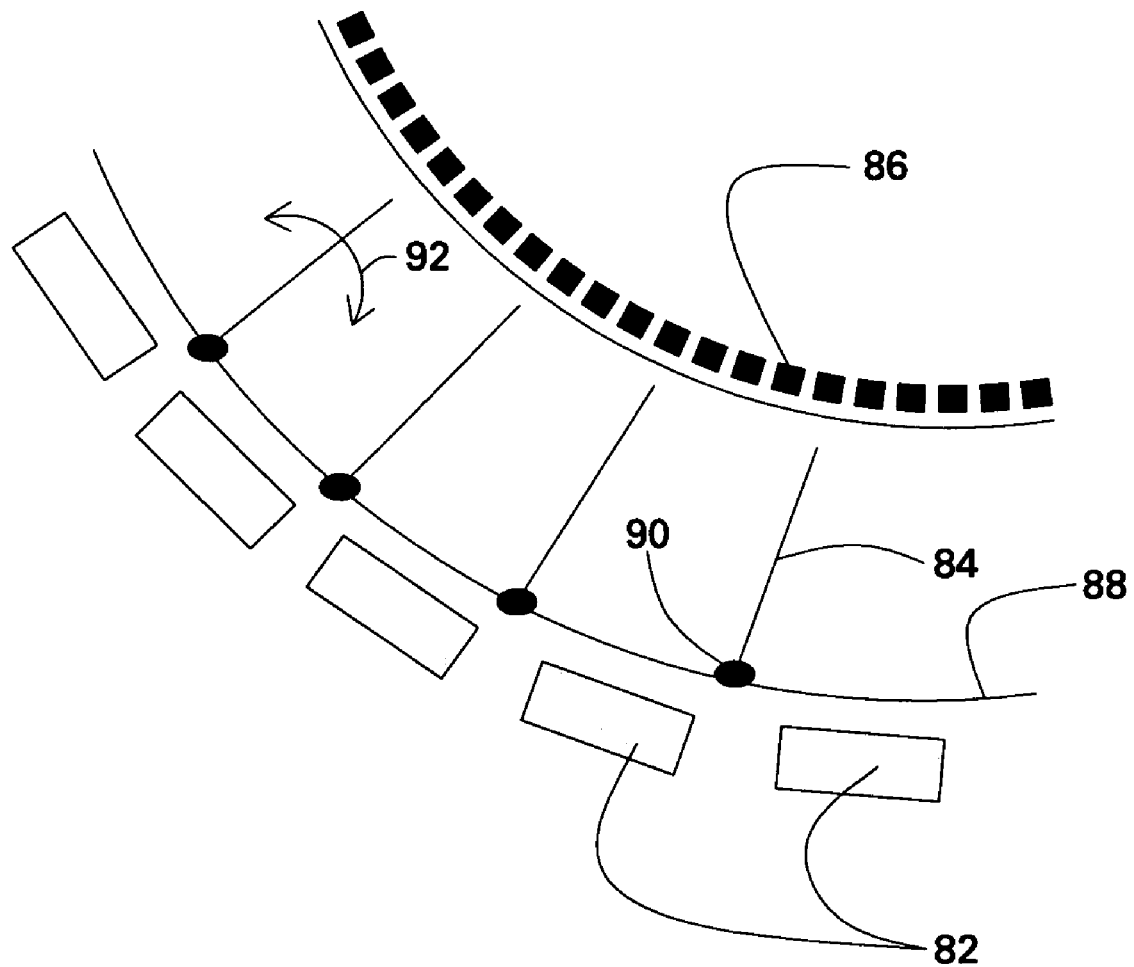
FIG. 8 is a diagrammatical representation of a further configuration having an electrostatically-controlled implementation for the configuration of FIG. 7.

FIG. 8 is a diagrammatical representation of a further configuration of a scatter reduction system having an electrostatically-controlled implementation for the above configuration where collimator septa 84 are hinged and angularly adjusted to maintain focal alignment, thereby reducing scatter measurements in detectors 82. The septa 84 in one example may be electrostatically aligned with respect to a given focal point, which is coincident with an X-ray focal spot location (not shown). Multiple electrodes 86 may be used, and these electrodes may be configured to be individually charged, to an opposite potential with respect to the septa 84. In operation, in one example, the series of septa 84 are electrostatically (or electromagnetically) aligned with the focal spot location. In a specific embodiment, the array of septa 84 hinged at 90 may be attached along a ring 88 that is immediately inside a ring containing detectors 82. To electrostatically control the septa 84, they may first be all charged to an equipotential voltage. The electrodes 86 may then be individually charged to an opposite potential so as to attract the septa 84. By controlling which electrodes 86 on the inner ring are charged, the angular orientation of the septa 84, indicated generally by the reference numeral 92, may be adjusted to point directly at the focal spot location. The use of electrostatic forces allows for easy and rapid control of the angular direction for an individual septum. Also, depending on the pitch of inner electrodes, fine-tuning of the angle of the septa may be achieved by charging different electrodes to different potentials. Since the moving parts, in the above described embodiment are limited to only the hinge 90 of the septa 84, there will be an added advantage of having a sufficiently long lifetime for this embodiment.

Typically, the septa 84 include at least a thin metal sheet or a metal coating disposed on a base material (for example, Mylar or thin Silicon since it is already flat and has some structural stiffness). Any high atomic number material may be used on the septa to absorb scattered X-rays. The high atomic number material may also be an electrically conductive material (Tungsten or Lead, for instance) that enhances the ability to charge the septa. The inner ring of electrodes 86 may be formed from a material that is relatively transparent to X-rays such as a thin aluminum coating on Silicon or graphite. The spacing of collimator septa 84 and positioning electrodes 86 is typically determined by the detector parameters. For example for current CT systems the septa spacing is approximately 1 mm. The method of building the hinge 90 depends on the spacing as well as the height of the septa 84. If the aspect ratio (height/spacing) is greater than 1, then the septa 84 might be made of metal vanes fitted in hinges 90. For aspect ratios less than 1, the septa 84 may be made from Lead or Tungsten coated Silicon that has been thinned and cut to allow for bending at the hinge point 90.

An alternate configuration consists of the hinged septa shown in FIG. 8 being constructed of a magnetic material such as Nickel or in some other way as to have a magnetic moment associated with it. Elements 86, in this embodiment, would then be small electromagnetically-controlled elements. The magnetic field generated by these elements would then control the movement of the septa 84 through attraction or repulsion via magnetic fields. Other statements about the electrostatic configuration such as focal spot alignment and hinging would also apply to this embodiment.

Figure 9:
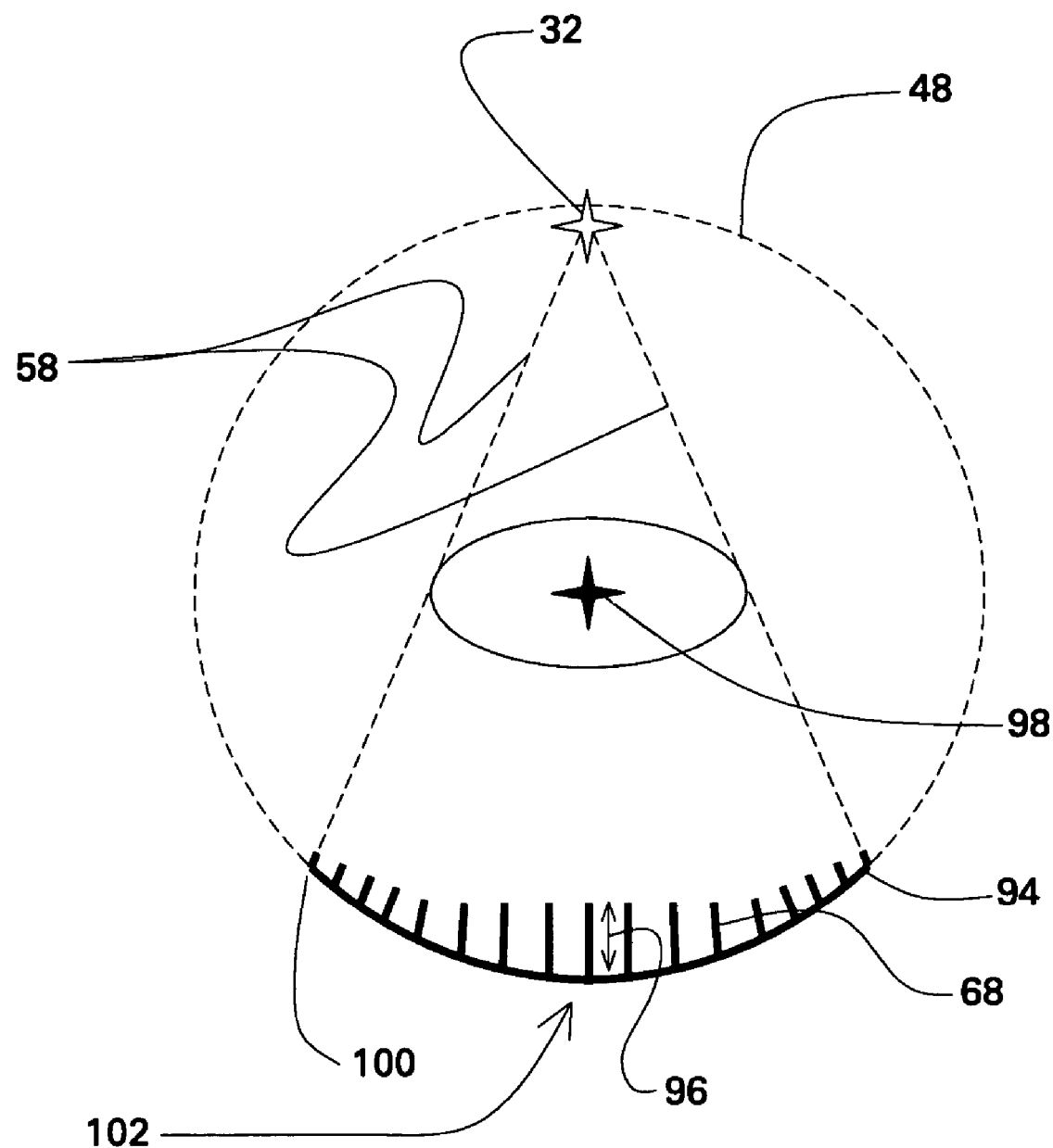
FIG. 9 is a diagrammatical representation of a further configuration with a plurality of collimator septa with varying heights in the anti-scatter grid.

FIG. 9 is a diagrammatical representation of a further configuration illustrating varying height 96 of each of the multiple of collimator septa 68 located at or near the detector surface 94. The collimator septa 68 correspond to an instantaneous field of view defined by the primary X-ray beam 58 and attenuate scatter generated from the at least one X-ray beam. The X-ray scatter is rejected in this configuration by the high atomic number of the material used for collimator septa 68 that are incrementally positioned just above the surface of the detector 48. The profile created by the height of the collimator septa is optimally designed so as to reject scatter with minimum attenuation of primary X-ray radiation. The movement of the profile over time assumes the appearance of a 'wave' that travels along an arc of the detector surface. In an exemplary embodiment the collimator septa are always focused to an isocenter position 98 (a fixed alignment relative to the detector normal) and the height 96 of the collimator septa 68 is modulated in concert with the movement of the X-ray focal spot location 32. The height of the collimator septa is smallest at the edge 100 of the instantaneous field of view (FOV) so that there is little attenuation of the primary X-ray beam. Attenuation of the scatter at this extreme location is also less. At the center 102 of the instantaneous field of view, the collimator septa assume their maximum height and provide good selectivity for primary X-ray beam radiation over scattered radiation. Although not shown, multiple arcs of collimator 68 may be used around the gantry 12 to reduce scatter resulting from the illumination of the instantaneous field of view with X-ray radiation generated from multiple X-ray focal spot locations 32, which may be activated sequentially, simultaneously, or in a predetermined sampling pattern, similar to an arrangement shown in FIG. 7.

Figure 10:
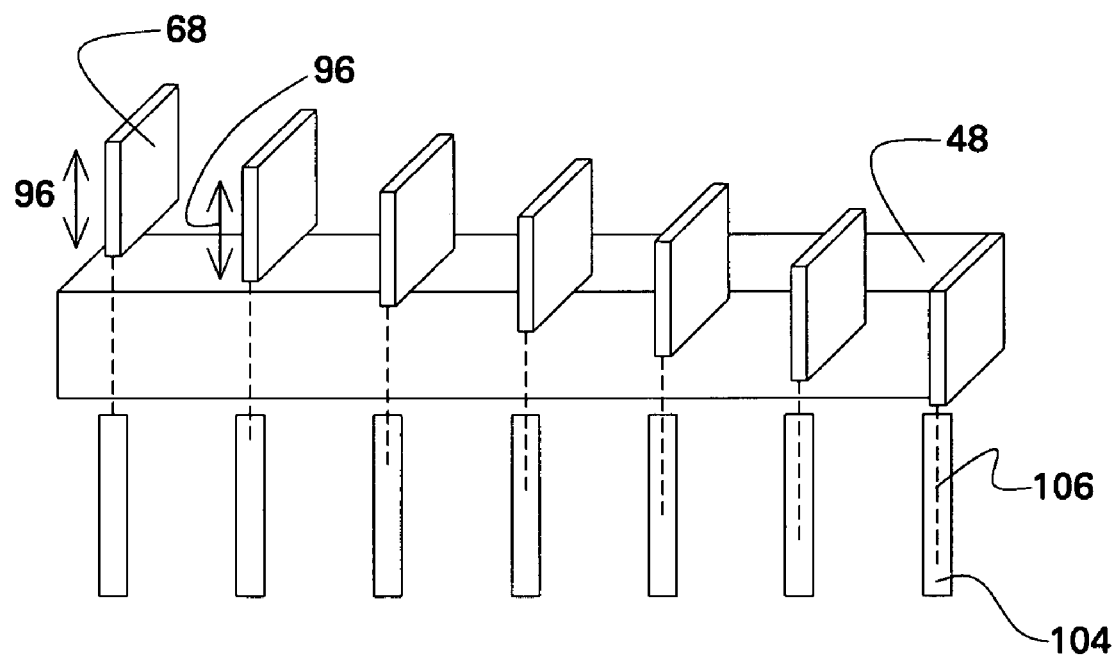
FIG. 10 is a diagrammatical representation of a further configuration having linear actuators for implementing the configuration of FIG. 9.

FIG. 10 illustrates an implementation of the above configuration using linear actuators 104. The linear actuators 104 are configured to move the collimator septa 68 via a linkage 106 to yield varying heights 96 for each of the collimator septa. Linear actuators 104 move each collimator septa 68 along a direction parallel to the detector normal (not shown) so as to modulate the height above the surface of the detector 48. This topology ensures that the profile of the collimators septa is maintained in coordination with the instantaneous position of the X-ray focal spot location (not shown), as described above. The linear actuators 104, in a specific example, include at least one of a mechanical actuator, a magnet actuator and a fluid actuator. Although the figure shows mechanical actuation as a means for translating the collimator septa 68, it will be well understood by those skilled in the art that magnetic or fluidic actuation could also be envisioned, as well as additional possibilities. Some of these exemplary implementation schemes are described below.

Figure 11:
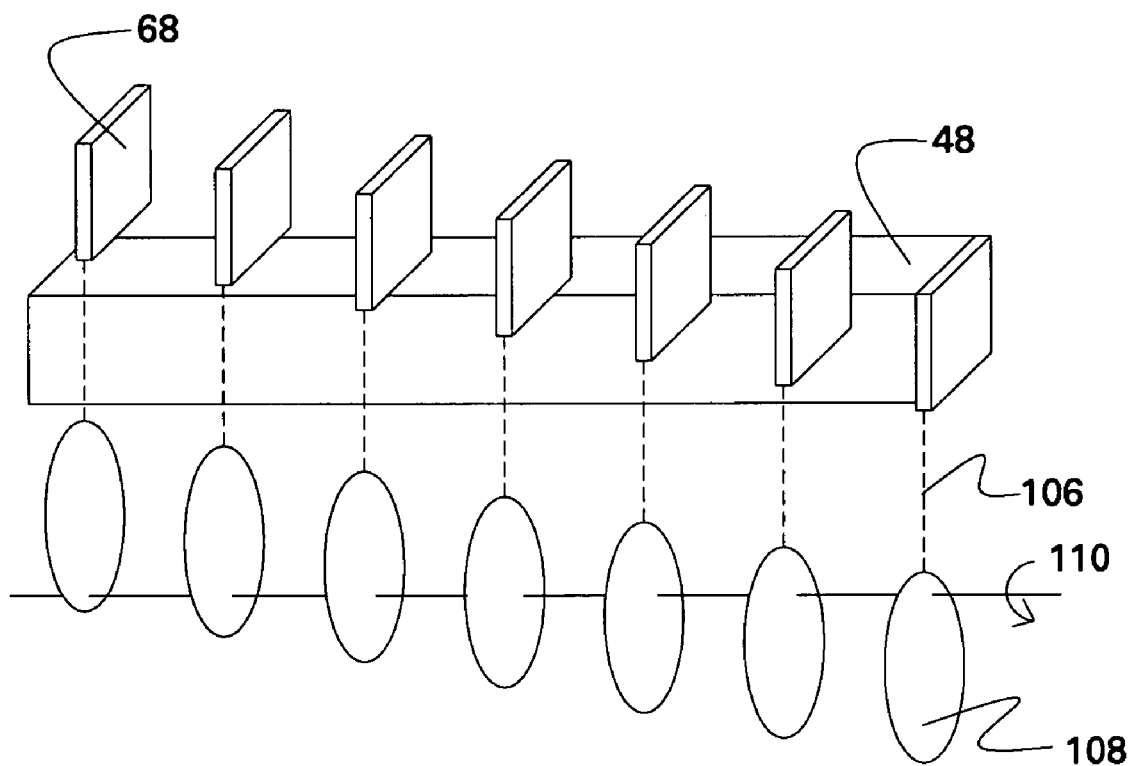
FIG. 11 is a diagrammatical representation of a further configuration having cams for implementing the configuration of FIG. 9.
Figure 12:
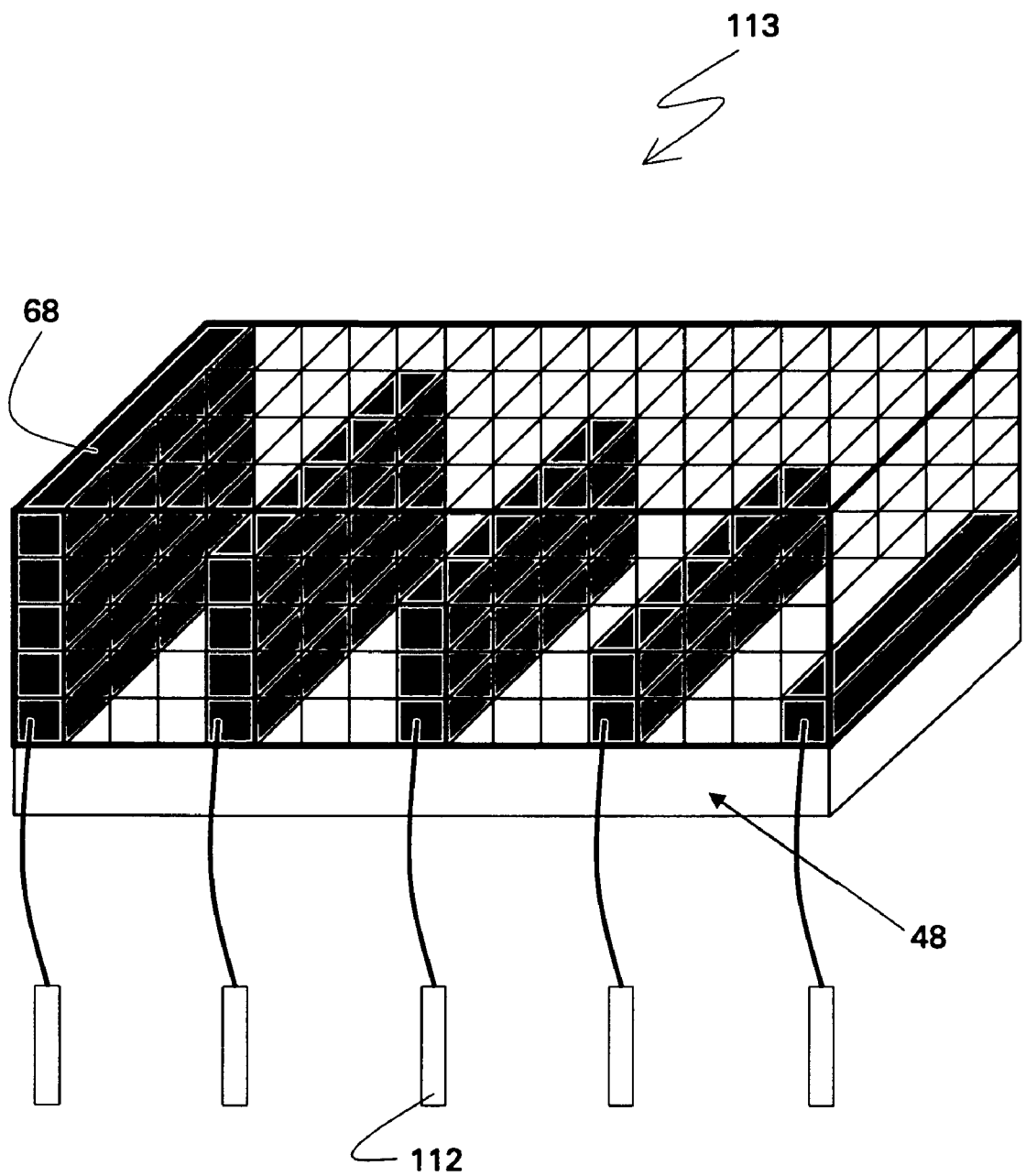
FIG. 12 is a diagrammatical representation of a further configuration having a fluidic implementation for the configuration of FIG. 9.

FIG. 11 illustrates a specific implementation scheme for the configuration of FIG. 10. A rotating axis 110 is connected near the perimeter of a circular disk (for example a cam) 108. A spring-loaded linkage 106 moves along the surface of the cam 108 to modulate the height of the collimator septa 68 above the surface of the detector 48. It will be appreciated by those skilled in the art that although FIG. 10 and FIG. 11 illustrate linear actuation, the shaft of the rotating axis 110 may be flexible and conform to the circular arc of the detector. Furthermore, the circular disk (or cam) 108 could comprise the collimator septa directly and move up and down relative to the rotating axis 110. FIG. 12 illustrates a fluidic implementation for the configuration of FIG. 10, where a bi-directional fluid pump 112 alternately fills and empties an enclosed vessel 113, the filled cells forming the collimator septa 68. The displacement of the fluid causes pressure differentials leading to different heights of septa 68 positioned across the stationary detector 48. As it would be well appreciated by those skilled in the art, the septa of FIG. 10, the cam of FIG. 11 and the fluid pump of FIG. 12 may receive control signals from the scatter control system 18 (as shown in FIG. 1) to adjust the height of the septa in accordance with the position of the source.

The various embodiments described hereinabove yield in the selective attenuation of scatter radiation over primary X-ray beam radiation in a way that accommodates a rotating X-ray source (or sequentially actuated source). This selectivity is advantageously used to enable collimation of non-rotating detector based CT systems. Specifically, the selectivity of the varying height collimator septa configuration allows flexibility in the degree of collimation introduced into the CT acquisition. For example, a larger object will tend to give a much larger scatter-to-primary ratio in measured X-ray intensity, and an aggressive collimation strategy is desirable. For smaller objects/patients where the scatter-to-primary ratio in the measured X-ray intensity is expected to be much lower, the collimation strategy could be designed to maximize the dose utilization while maintaining image quality. Thus the above described collimation schemes may be tailored to the imaging application based on expected scatter-to-primary ratios in the measured X-ray intensity. The above described embodiments facilitate the reduction of scatter in stationary detector systems, thus enabling very fast scanning without the drawback of increased scatter and its impact on image quality. As mentioned with other scatter control mechanisms, the arrangements shown in FIG. 9 to FIG. 12 may be rotated or stationary with requisite extent for the desired imaging application.

When using high-resolution detectors, it may not be feasible to collimate each detector cell. In these configurations, a reasonable spacing of collimator septa is chosen to appropriately reduce scatter while mitigating corruption of the projection data and improving dose efficiency.

Figure 13:
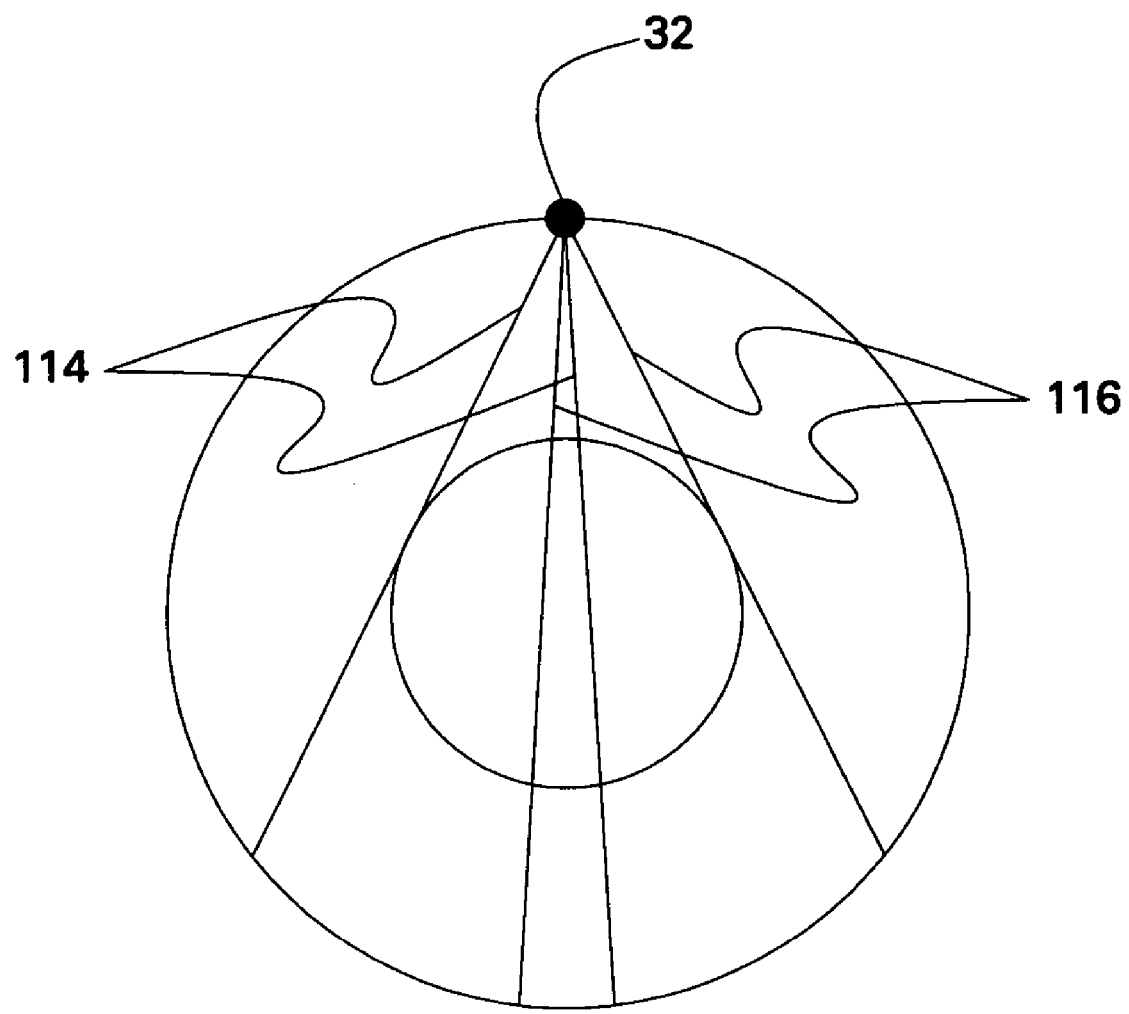
FIG. 13 is a diagrammatical representation of a further configuration for scatter control according to aspects of present technique, in which the X-ray beam is split into a plurality of smaller beams to reduce the scatter contributions.

FIG. 13 illustrates yet another technique for reducing scatter by splitting the X-ray fan-beam from the X-ray focal spot location 32 into two or more sub-beams 114 and 116. Because each sub-beam illuminates a smaller volume of the object being scanned, the scatter signal is correspondingly reduced. This splitting of the beam could be achieved in one example, by appropriately collimating the focal spot location 32. Splitting of the X-ray beam can be performed in an in-plane direction (as shown in FIG. 13) or in any other direction, such as the longitudinal direction (not shown).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An imaging system comprising:
   at least one stationary detector extending generally around at least a portion of an imaging volume;
   at least one distributed X-ray source placed proximal to the at least one stationary detector for radiating at least one X-ray beam toward the at least one stationary detector; and
   a scatter control system configured to adaptively operate in cooperation with the at least one stationary detector and the at least one distributed X-ray source to provide X-ray beam scatter control;
   wherein the scatter control system comprises an anti-scatter grid, the anti-scatter grid comprises a plurality of collimator septa extending around at least a portion of the at least one stationary detector, and wherein a height of each of the plurality of collimator septa is varied corresponding to an instantaneous field of view to attenuate scatter generated from the at least one X-ray beam.

2. The imaging system of claim 1 wherein the height of a collimator septa varies from a first height at an edge of the instantaneous field of view to a second height at a center of an instantaneous field of view, and wherein the first height is less than the second height.

3. The imaging system of claim 1 wherein the height of the plurality of collimator septa are modulated in concert with movement of a focal spot location generating the at least one X-ray beam.

4. The imaging system of claim 1 further comprising one or more linear actuators configured to move the plurality of collimator septa to yield varying heights for each of the plurality of collimator septa.

5. The imaging system of claim 4 wherein the one or more linear actuators comprise at least one of a mechanical actuator, a magnet actuator and a fluid actuator.

6. An imaging system comprising:
   at least one stationary detector extending generally around at least a portion of an imaging volume;
   at least one distributed X-ray source placed proximal to the at least one stationary detector for radiating at least one X-ray beam toward the at least one stationary detector; and a scatter control system configured to adaptively operate in cooperation with the at least one stationary detector and the at least one distributed X-ray source to provide X-ray beam scatter control;

wherein the scatter control system comprises an anti-scatter grid, the anti-scatter grid comprises a plurality of collimator septa extending around at least a portion of the at least one stationary detector, and wherein the plurality of septa are electrostatically positioned to be aligned with respect to X-ray beam generated from the at least one distributed X-ray source and wherein an angle for each of the plurality of collimator septa is modulated in concert with movement of a focal spot location for generation of the at least one X-ray beam.

7. The imaging system of claim 6 wherein one or more collimator septa from amongst the plurality of collimator septa within an X-ray beam path are configured to angularly adjust to focally align the plurality of collimator septa to the at least one X-ray beam.

8. The imaging system of claim 6 wherein one or more collimator septa from amongst the plurality of collimator septa not within an X-ray beam path, are configured to angularly adjust a respective collimator position to prepare for alignment during subsequent generation of the at least one X-ray beam enabling full illumination of an instantaneous field of view.

9. The imaging system of claim 6 wherein the plurality of septa comprise at least one of metal sheets and a metal coating deposited on a base material.

10. The imaging system of claim 6 further comprising a plurality of electrodes configured to be individually charged to an opposite potential with respect to the plurality of septa.

11. The imaging system of claim 6 wherein the plurality of septa are electromagnetically positioned to be focally aligned with respect to the X-ray beam generated from the at least one distributed X-ray source.

12. The imaging system of claim 6 further comprising a plurality of electromagnetic elements configured to create a magnetic field that can attract or repel the septa.

13. The imaging system of claim 6 wherein the scatter control system operates to split the X-ray beam into at least two sub-beams for reducing scatter.

14. An imaging system comprising:
at least one stationary detector extending generally around at least a portion of an imaging volume;
at least one distributed X-ray source placed proximal to the at least one stationary detector for radiating at least one X-ray beam toward the at least one stationary detector;
an anti-scatter grid adapted to focally align a plurality of collimator septa contained therein to a plurality of focal spot locations generating a plurality of X-ray beams, wherein a height of each of the plurality of collimator septa is varied corresponding to an instantaneous field of view to attenuate scatter generated from the at least one X-ray beam.

15. An imaging system comprising:
at least one stationary detector extending generally around at least a portion of an imaging volume;
at least one distributed X-ray source placed proximal to the at least one stationary detector for radiating at least one X-ray beam toward the at least one stationary detector; and
an anti-scatter grid comprising a plurality of collimator septa extending around at least a portion of the at least one stationary detector, wherein a height of each of the plurality of collimator septa is varied corresponding to an instantaneous field of view to attenuate scatter generated from the at least one X-ray beam.

16. The imaging system of claim 15 wherein the height of a collimator septa varies from a first height at an edge of the instantaneous field of view to a second height at a center of an instantaneous field of view, and wherein the first height is less than the second height.

17. The imaging system of claim 15 wherein the height of the plurality of collimator septa is modulated in concert with movement of a focal spot location generating the at least one X-ray beam.

18. A scatter control system for use in an imaging system having at least one stationary detector extending generally around at least a portion of an imaging volume and at least one distributed X-ray source placed proximal to the at least one stationary detector for radiating at least one X-ray beam toward the at least one stationary detector, the scatter control system comprising:
an anti-scatter grid adapted to focally align a plurality of collimator septa contained therein to X-ray beams from multiple focal spot locations, wherein the anti-scatter grid comprises a plurality of collimator septa extending around at least a portion of the at least one stationary detector,
wherein a height of each of the plurality of collimator septa is varied corresponding to an instantaneous field of view to attenuate scatter generated from the at least one X-ray beam.

19. A method of imaging, comprising:
sequentially firing at least one distributed X-ray source for radiating at least one X-ray beam toward at least one stationary detector;
focally aligning a plurality of collimator septa contained therein with the at least one X-ray beam using a scatter control system in cooperation with the at least one stationary detector and the at least one distributed X-ray source, wherein the scatter control system comprises an anti-scatter grid adapted to focally align to a plurality of X-ray beams emanating from multiple focal spot locations; and
varying a height of each of the plurality of collimator septa corresponding to an instantaneous field of view to attenuate scatter generated from the at least one X-ray beam.

20. The method of claim 19 further comprising modulating the height of the plurality of collimator septa in concert with movement of a focal spot location generating the at least one X-ray beam.

* * * * *